United States Patent
Duckett et al.

(10) Patent No.: US 6,550,487 B1
(45) Date of Patent: *Apr. 22, 2003

(54) APPARATUS FOR REMOVING DEPOSITS FROM ENCLOSED CHAMBERS

(75) Inventors: Michael A. Duckett, Erie, PA (US); John C. Bliley, Erie, PA (US); Gerald J. Kielar, Erie, PA (US); Sayed Sadiq Shah, St.Louis, MO (US); Anthony W. Raymond, San Diego, CA (US)

(73) Assignee: Steris Inc., Temecula, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/522,267

(22) Filed: Mar. 9, 2000

(51) Int. Cl.$^7$ .............................. B08B 3/08; B08B 9/00
(52) U.S. Cl. ............................ 134/22.18; 134/22.17; 134/22.19; 134/22.1; 134/26; 134/27; 134/28; 134/29; 134/36; 134/41; 134/95.03; 134/108; 134/168 R
(58) Field of Search ................ 134/22.18, 22.19, 134/24, 26, 27, 28, 29, 36, 41, 22.17, 95.03, 107, 108, 168 R, 169 R

(56) References Cited

U.S. PATENT DOCUMENTS

| | | |
|---|---|---|
| 2,448,045 A | 8/1948 | Pegg |
| 3,077,454 A | 2/1963 | Monroe |
| 3,195,546 A | 7/1965 | Tonkowich et al. |
| 3,308,065 A | 3/1967 | Lesinski |
| 3,413,160 A | 11/1968 | Tenmae |
| 3,438,811 A | 4/1969 | Harriman |
| 3,506,576 A | 4/1970 | Teumac |
| 3,549,538 A | 12/1970 | Jacklin |
| 3,593,728 A | 7/1971 | Sauer |
| 3,865,628 A | 2/1975 | Callahan et al. |
| 4,402,331 A | 9/1983 | Taldo et al. |
| 4,454,046 A | 6/1984 | Wallace et al. |
| 4,653,518 A | 3/1987 | Adachi |
| 5,039,349 A | 8/1991 | Schoeppel |
| 5,766,684 A | 6/1998 | Shah et al. |
| 5,858,118 A | 1/1999 | Shah et al. |
| 6,341,612 B1 * | 1/2002 | Duckett et al. ............ 134/95.1 |

FOREIGN PATENT DOCUMENTS

| | | |
|---|---|---|
| DE | 41 14 951 A1 | 11/1992 |
| DE | 43 12 417 A1 | 10/1994 |
| EP | 0 086 245 A | 8/1983 |

OTHER PUBLICATIONS

Jellinke: Reinigen von Chromnickelstahl: Galvanotechnik., vol. 76, No. 9 Sep. 1, 1985, Saulgau/Wurtt DE, pp. 1251 XP002060316.

Handbook & Chemistry and Physics, 56th Ed., "Standard Types of Stainless and Heat Resisting Steels".

NACE Publication on "Corrosion Basics An Introduction," pp. 41–42, 1984.

J.C. Scully, "The Fundamentals of Corrosion" pp. 112–123.

E.C. Rollason, "Metallurgy for Engineers" Fourth Edition, pp. 246–248.

Gosta Wranglen, "An Introduction to Corrosion and Protection of Metals" pp. 78–83.

* cited by examiner

Primary Examiner—Zeinab El-Arini
(74) Attorney, Agent, or Firm—Fay, Sharpe, Fagan, Minnich & McKee, LLP

(57) ABSTRACT

A cleaning unit (A) includes a movable cart (20) which carries a cleaning system for cleaning baked-on residues from walls (10) of a sterilizer chamber (12). The cleaning system includes a lid (80) which is mounted over an opening (82) to the chamber. In one embodiment, the door (232) of the chamber provides the lid. An articulating nozzle (124) extends from the lid into the interior of the chamber. Alkaline and acid cleaning solutions (180, 182), for removing organic and inorganic residues, respectively, from the chamber, are stored in two storage containers (52, 54) carried by the cart. A first pump (60), mounted on the cart, pumps first the alkaline, then the acid cleaning solution to the nozzle. A second pump (62), mounted on the cart, connects with a scavenge fitting (166) in the chamber to return the cleaning fluid to the respective storage container. After cleaning is complete, the two cleaning fluids are mixed together to form a neutral or near neutral solution which is disposable in a sanitary sewer system without further treatment.

29 Claims, 7 Drawing Sheets

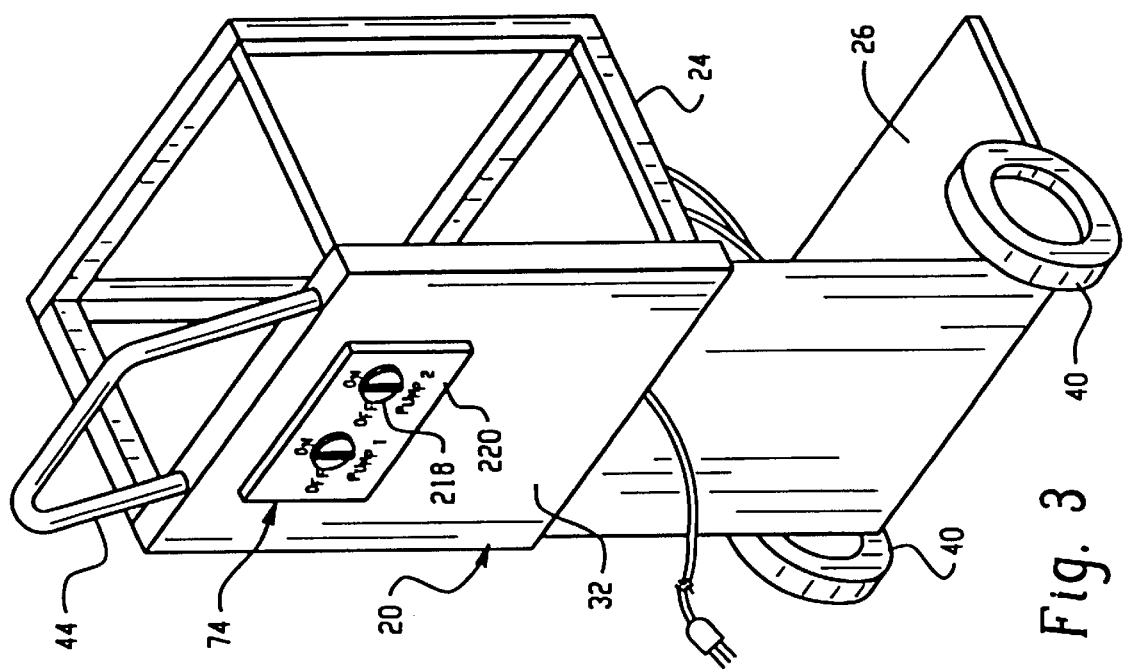
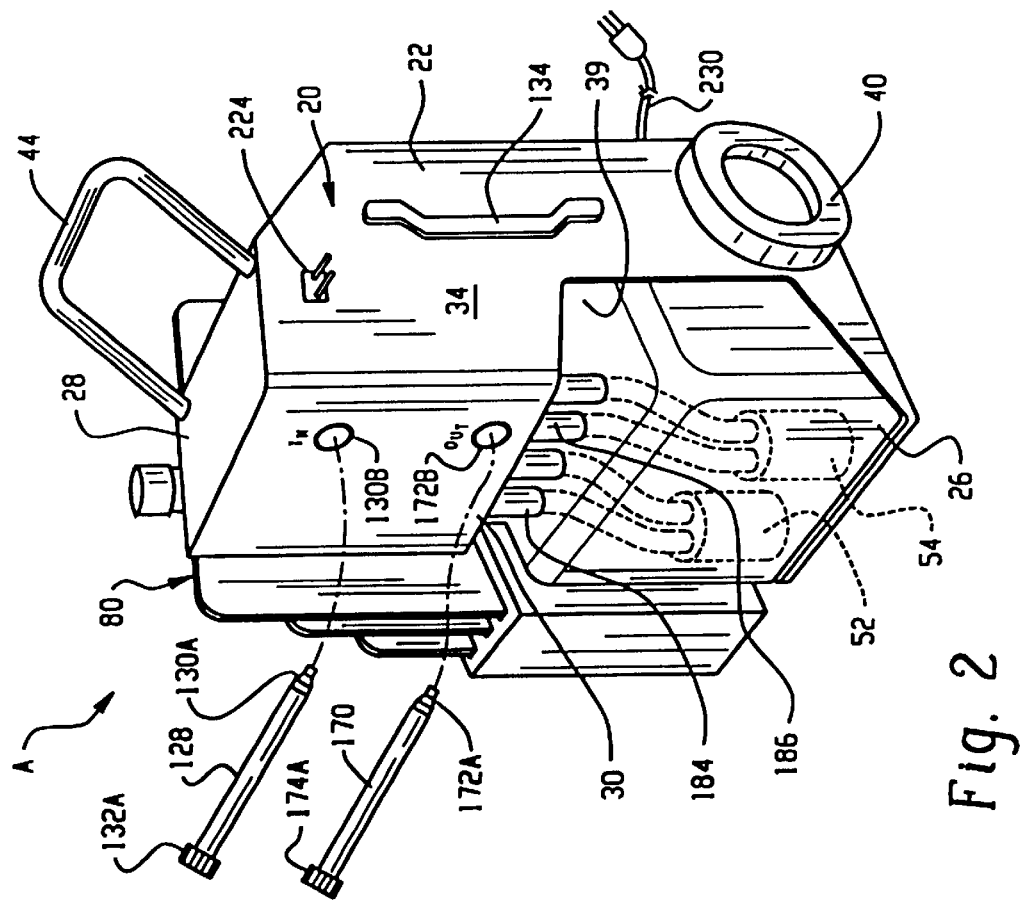

APPARATUS FOR REMOVING DEPOSITS FROM ENCLOSED CHAMBERS

BACKGROUND OF THE INVENTION

The present invention relates to the chemical leaning arts. It finds particular application in conjunction with the removal of baked on residues from sterilizers, and will be described with particular reference thereto. It should be appreciated, however, that the invention is also applicable to the cleaning of residues from other processing equipment, such as pharmaceutical, food, and beverage equipment, and the like.

Steam sterilizers are generally operated at a pressure of about 2 kg/sq. cm (30 psi) and a temperature of around 130° C. Over a period of time, the chamber walls become coated with a residue comprising baked on materials, such as boiler compounds, lint, debris, tape and packaging materials used to wrap medical devices being sterilized. These residues interfere with the efficient operation of the sterilizer or may be dislodged from the chamber walls and soil the sterilized items.

The baked on residues are difficult to remove. Mechanical methods have been used to remove the residue, but these are labor intensive. It takes approximately 6–8 hours to mechanically clean one sterilizer. In one method, the chamber walls are blasted with a stream of glass beads. An air compressor, which is parked outside the facility and connected to the glass bead equipment by a long air line, powers the equipment. The chamber is tented to contain the beads and dust generated. A ventilation hood, supplied by a separate air compressor, is worn by the operating technician. The surface of the chamber walls is often left in a roughened condition which is difficult to polish to a smooth finish.

In another method, a hand-held grinding/polishing wheel and an abrasive compound are used to remove the residue. The grinding wheel is usually powered by an air compressor, as for the glass bead method. The sterilizer is tented to contain dust generated in the process and breathing equipment is worn by the technician performing the cleaning. In the process, weld joints and studs in the sterilizer may be damaged and additional time is taken to repair the damage. For nickel plated sterilizer chambers, the polishing process may remove the thin nickel plating (typically around 0.5 millimeter in thickness, or less) exposing the underlying carbon steel to subsequent corrosion. On stainless steel sterilization chambers, damage to weld joints is a problem.

The present invention provides a new and improved apparatus and method for cleaning baked-on residue from a vessel which overcomes the above-referenced problems and others.

SUMMARY OF THE INVENTION

In accordance with one aspect of the present invention, an apparatus for removing baked on residues from a sterilizer chamber is provided. The apparatus includes a moveable cart, a supply of cleaning fluid carried by the cart, a lid mountable across an opening to the sterilizer, and a nozzle mounted to the lid for spraying the cleaning fluid into the chamber. A first fluid supply line fluidly connects the source of cleaning fluid with the nozzle. A first pump is carried by the cart and is fluidly connected with the first fluid line for pumping the cleaning fluid to the chamber. An outlet is provided in the lid through which sprayed cleaning fluid can be withdrawn from the chamber. A second fluid supply line is fluidly connected with the outlet. A second pump is carried by the cart and is fluidly connected with the second fluid line for pumping the cleaning fluid from the chamber.

In accordance with another aspect of the present invention, an apparatus for removing baked on organic residues and inorganic residues from a chamber is provided. The apparatus includes a first cleaning fluid reservoir, which holds a first cleaning fluid for removing organic residues and passivating the chamber. A second cleaning fluid reservoir holds a second cleaning fluid for removing inorganic residues and passivating the chamber. A nozzle is provided for spraying the cleaning fluid into the chamber. A first fluid supply line fluidly connects the first and second cleaning fluid reservoirs of cleaning fluid with the nozzle. A first pump is fluidly connectable with the nozzle and the first and second cleaning fluid reservoirs for pumping the cleaning fluid to the chamber. A second pump is fluidly connectable with the chamber for pumping the cleaning fluid from the chamber.

In accordance with another aspect of the present invention, a method of removing baked on residues from a sterilizer chamber is provided. The method includes mounting a lid over an opening to the chamber such that a nozzle mounted to the lid extends into the interior of the chamber. Further, the method includes pumping a first cleaning fluid from a first source of cleaning fluid to the nozzle, spraying the first cleaning fluid from the nozzle over walls of the chamber, and pumping the sprayed first cleaning fluid from the chamber.

One advantage of the present invention is the provision of an easily portable cleaning system.

Another advantage of the present invention is that a sterilizer is cleaned and ready to be returned to service in about two to four hours.

Yet another advantage of the present invention is that the cleaning compositions are contained within the system and pose few hazards to operating technicians.

A further advantage of the present invention is that a neutralized product is formed after cleaning which may be disposed in the normal waste system.

A yet further advantage of the present invention is that the cleaning compositions have no significant impact on the nickel plate on the sterilizer walls.

A still yet further advantage of the present invention is that the system is adaptable to a variety of sterilizer shapes and sizes.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2 is a side perspective view of the equipment housing of the system of FIG. 1;

FIG. 3 is a rear perspective view of the equipment housing of FIG. 2 with some of the housing panels removed;

DETAILED DESCRIPTION OF THE PREFERRED EMBODIMENTS

Figure 1:
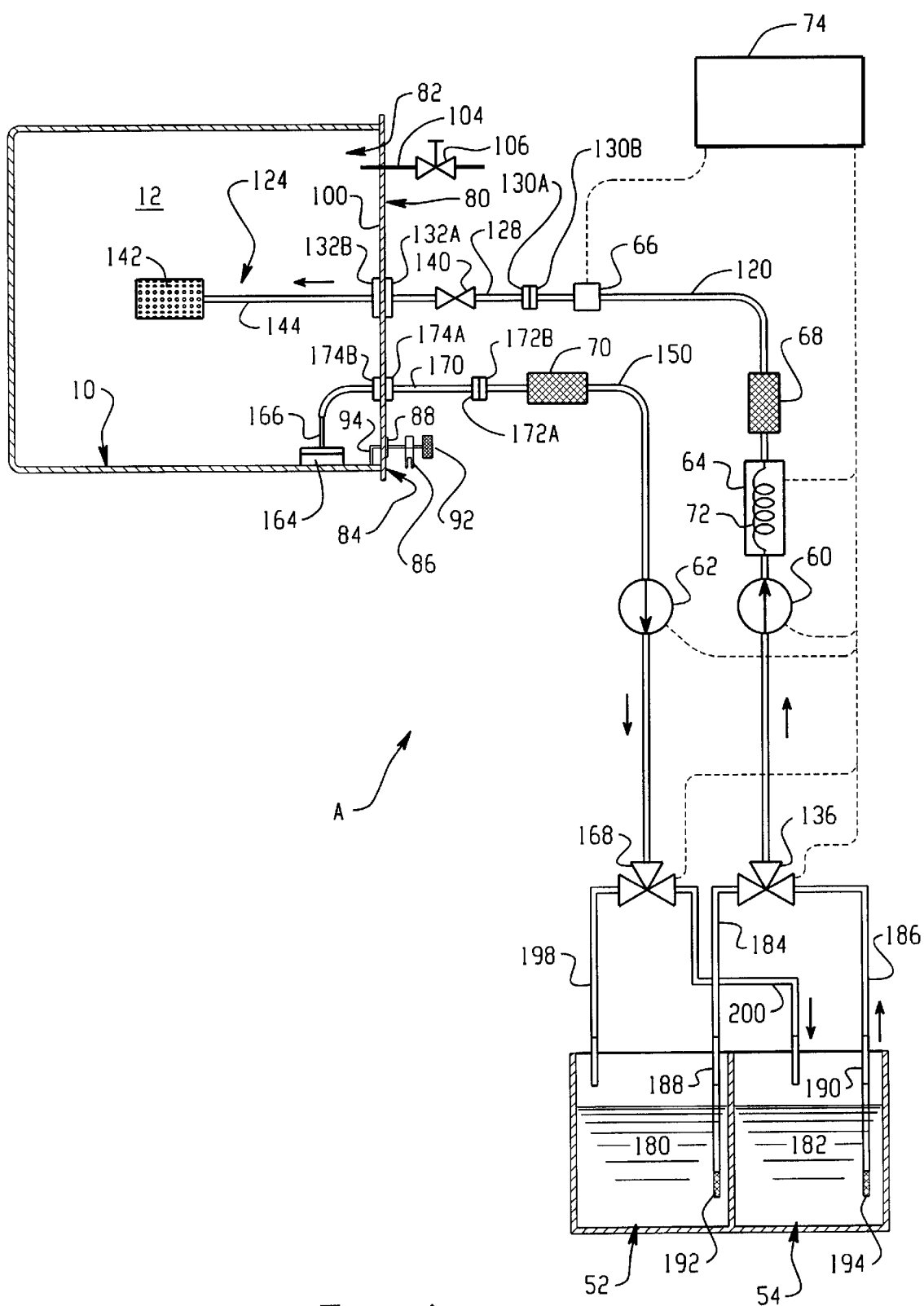
FIG. 1 is a schematic view of a cleaning system in position on a sterilizer, in accordance with a first embodiment of the present invention.

With reference to FIGS. 1 and 2, a portable system A for cleaning residues from the interior walls 10 of a sterilizer chamber 12 is shown. The system is particularly suited for cleaning nickel clad sterilizer chamber walls, although it may also be used for cleaning stainless steel sterilizer chambers.

Figure 4:
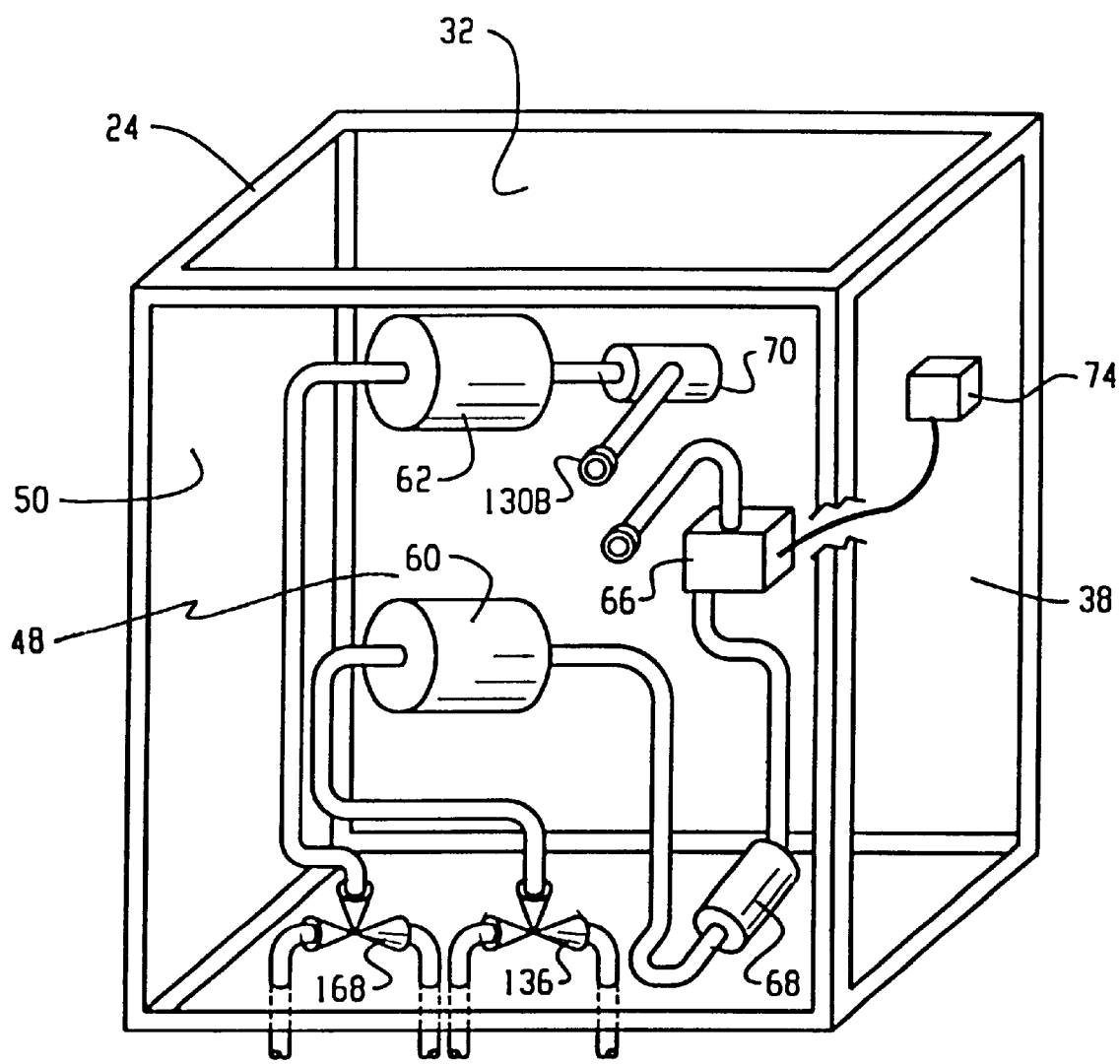
FIG. 4 is a front perspective view of the equipment housing of FIG. 2 with the housing panels removed.
Figure 5:
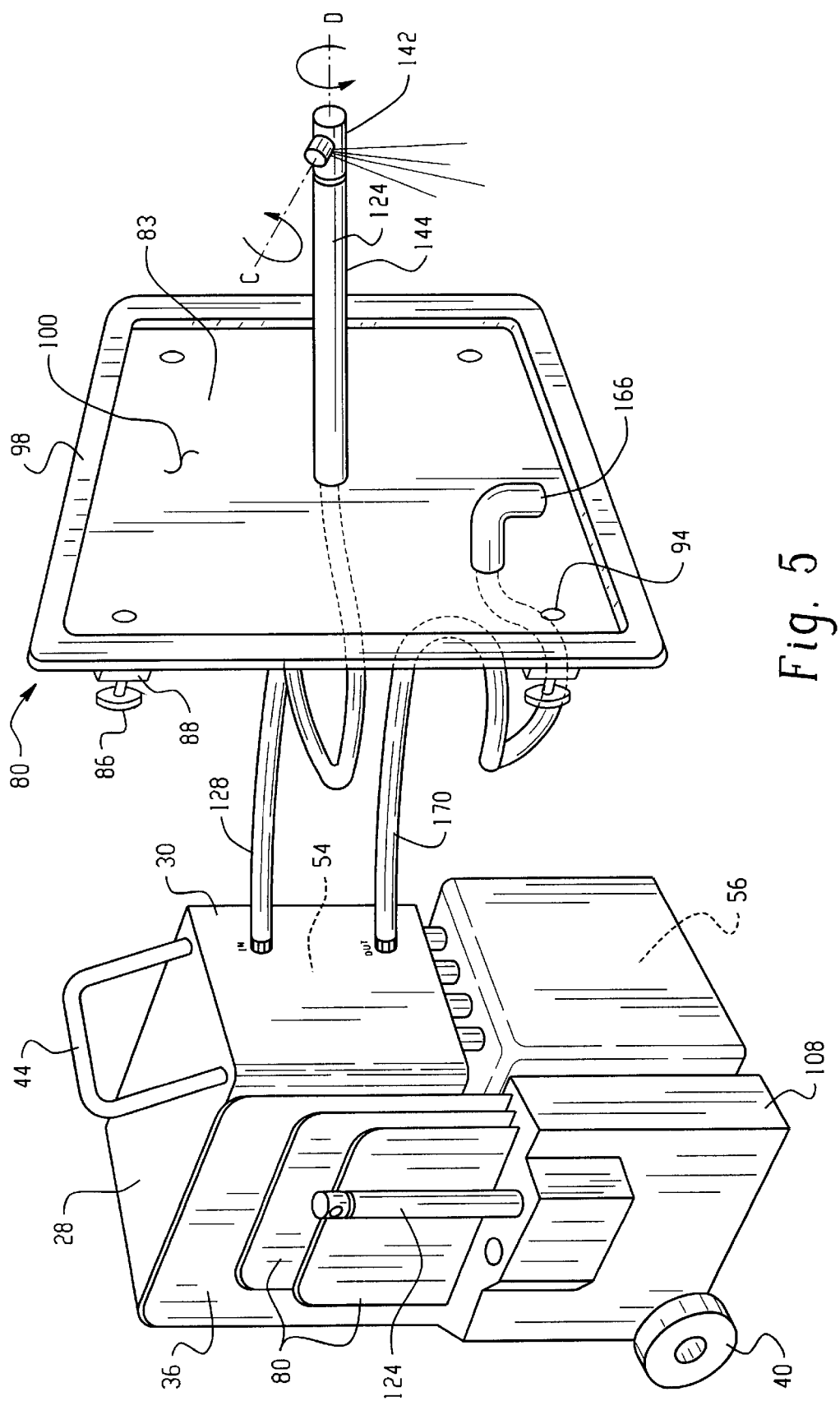
FIG. 5 is a perspective view of the cleaning system of FIG. 1.

With reference also to FIGS. 3–5, the system A includes a cart 20 for transporting the system to the sterilizer to be cleaned. The cart includes a housing 22 with an interior support frame 24 and a base shelf 26, a top 28, and four housing panels, namely, an upper front panel 30, a rear panel 32, and two side panels 34 and 36, respectively. The rear, left, and right side panels 32, 34, extend generally vertically between the base and the top and form the rear, and left and right sides of the housing, respectively. The front panel 30 cooperates with the top, side, and rear panels to form a housing enclosure or upper compartment 38. The front panel extends only part way down the front of the cart to provide access to a tank storage area or lower compartment 39 below the housing enclosure, as shown in FIG. 2. Two (or more) spaced wheels 40 are mounted to a rear end of the housing adjacent the base 26 for maneuvering the cart around a facility. Additional wheels may be positioned at the front of the cart for improved stability. A handle 44, mounted to the top of the housing is used for directing the cart.

The housing 22 holds the operating equipment 48 of the system A in the upper compartment 38 and one or more reservoirs or tanks 52, 54 of cleaning fluid in the lower compartment 39. The reservoirs comprise disposable or refillable containers which are filled with cleaning solutions. The containers are formed from a relatively rigid material, such as plastic, which is not degraded by the cleaning solutions at the temperatures used.

With particular reference to FIGS. 1 and 4, the operating equipment 48 includes a high pressure pump 60 for pumping a selected cleaning solution to the chamber 12 of the sterilizer and a scavenge pump 62 for removing the cleaning solution from the chamber. The operating equipment also includes an in-line heater 64, a temperature sensor 66, and, optionally, inlet and outlet strainers or filters 68 and 70, respectively, for filtering particles of dirt from the cleaning solution. As shown in FIG. 1, the heater 64 includes a heating coil 72, which heats the cleaning solution to a suitable temperature for cleaning, preferably about 55–70° C. at the sterilizer chamber walls, although other methods of heating and heating temperatures are also contemplated. The temperature sensor 66 measures the temperature of the cleaning solution just prior to it entering the sterilizer. A control system 74, such as a computer control system or other solid state control system, receives temperature signals from the sensor 66 and regulates the in-line heater 64 accordingly. As shown in FIG. 3, the control system 74 is mounted to the outside of the housing on the rear panel 32, although other suitable locations are also contemplated.

Figure 6:
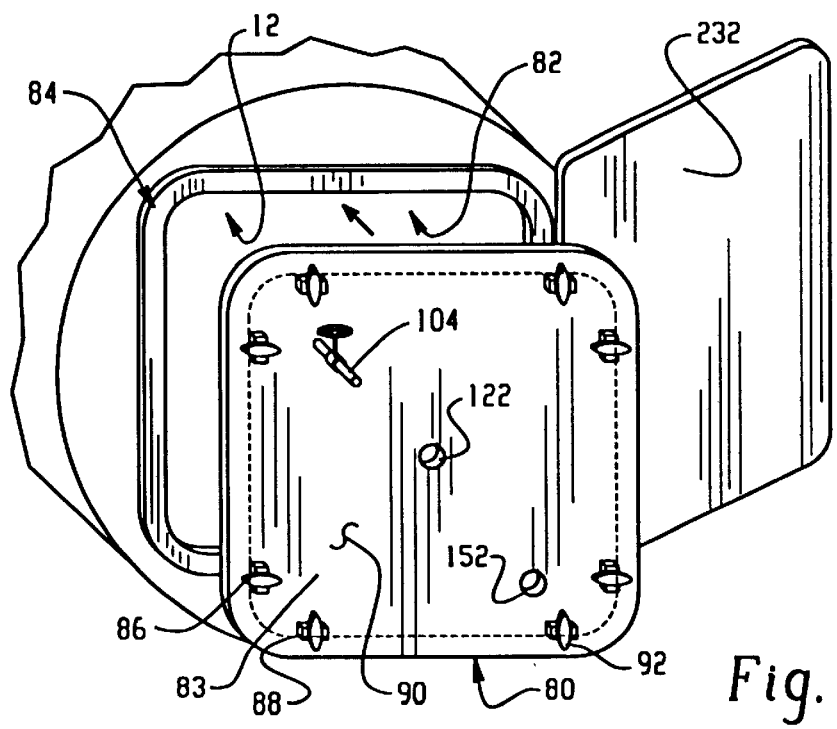
FIG. 6 is a front perspective view of a sterilizer with the lid of the system of FIG. 5 positioned for attachment over the opening.

With particular reference to FIGS. 5 and 6, a demountable lid 80 closes an opening 82 in the sterilizer chamber during cleaning. As best shown in FIG. 6, the lid includes a flat plate 83 which is fixed to an end ring 84 of the sterilizer by fixing members, such as clamping bolts 86. The end ring is typically formed from monel and is not exposed to the conditions within the sterilizer chamber 12 during sterilization. Thus, it remains relatively free from tarnish or deposits. The bolts include blocks 88, which are fixed to an outer surface 90 of the lid plate 83. The blocks are spaced from the outer edge of the lid plate. Swivel headed screws 92, tapped through the blocks and lid plate, turn threaded feet 94 mounted to the screws on the inside of the lid plate until they engage the inside surface of the end ring 84 of the sterilizer to position the lid.

A suction-tight fit between the end ring 84 and the lid 80 is provided by the scavenger pump 62. Specifically, during cleaning, the scavenger pump is set to create a sub-atmospheric pressure within the sterilizer chamber (i.e., a slight negative pressure), thus sealing the lid 80 against the end ring 84. This provides containment of the cleaning solutions and their vapors. To achieve the pressure differential, the scavenger pump 62 pumps the cleaning solution out of the chamber 12 at a higher rate than the high pressure pump 60 pumps it in. Optionally, a sealing member 98, such as a gasket, is fitted between the end ring and the lid. Preferably, the gasket is glued, or otherwise attached to an inside surface 100 of the lid plate around the perimeter thereof. An air bleed line 104, with a valve 106, is connected with the lid plate 83 for releasing the pressure inside the chamber 12 once cleaning is complete to facilitate removal of the lid.

The lid plate 83 is sized according to the size of the chamber opening 82. Commercial sterilizers often have openings of 16"×16" (about 40 cm×40 cm), 20"×20" (about 50 cm×50 cm), or 24"×36" (about 60 cm×90 cm). Accordingly, it is desirable to provide several, interchangeable lids 80 of different plate sizes for servicing different size chambers. Preferred lid plates are formed from plastic or stainless steel and have a thickness of about 0.3–1.0 cm. The lids are stored on the cart 20 when not in use. As shown in FIGS. 2 and 5, a storage bin 108 is mounted for this purpose on the side panel 36 of the cart, although it is also contemplated that the bin could also be accommodated on the rear or front panels of the housing 22.

With reference once more to FIGS. 1, 5, and 6, a first, or inlet fluid line 120 carries the cleaning solution from a selected one of the cleaning solution reservoirs 52, 54 via the high pressure pump 60, the heater 64, and the temperature sensor 66, to the lid 80. The heater preferably heats the fluid to a temperature suitable for cleaning the sterilizer, generally above about 18° C. The inlet fluid line passes through a first, centrally opening 122 in the lid plate 83 to a nozzle 124 releasably mounted to the chamber side 100 of the lid plate. When not in use, the nozzle 124 is stored in the storage bin 108, as shown in FIG. 5.

With particular reference to FIGS. 2 and 5, a disconnectable portion 128 of the first fluid line 120 between the housing 22 and the lid 80 is preferably formed from a length of flexible hose with quick connector couplings 130A, 132A at first and second ends, respectively, for quickly connecting with corresponding quick connector couplings 130B and 132B, on the front panel 30 of the housing and on the lid 80, respectively. When not in use, the hose 128 is uncoupled from the lid and the housing quick connectors 132B, 130B and stored on a hose reel 134 mounted on one of the side panels 34 of the housing, as shown in FIG. 2.

A first three way valve 136, such as a directional ball valve, in the fluid inlet line 120 is fluidly connected between the two cleaning solution reservoirs 52, 54 and the high pressure pump 60 for selectively delivering cleaning solution from one of the cleaning solution reservoirs 52, 54 to the chamber 12. Optionally, a manually operated valve 140 in the fluid inlet line 120 allows the inlet line to be closed, in case of accidental leakage of fluid, such as from the sterilizer chamber.

With particular reference to FIG. 5, the nozzle 124 sprays the cleaning solution over the walls 10 of the sterilizer chamber. A preferred nozzle is one which systematically sprays the entire surface of the chamber walls such that an even coverage of the cleaning solution is obtained. The nozzle may have one or more spray heads 142. A particularly preferred nozzle includes an articulating spray head 142, which is articulated for rotation about two perpendicular axes C, D (i.e., it rotates in three axes). The articulation is powered by the pressure of the cleaning solution entering the nozzle 124, such that over a period of a few minutes, the spray head 142 makes a series of rotational passes which provide complete coverage of the chamber walls 10. The nozzle includes a rigid tubular portion 144 which releasably connects the spray head with the interior surface 100 of the lid plate by quick connect 132B, or other convenient means. The tubular portion 144 is of a suitable length for positioning the spray head 142 at or near the center of the sterilizer chamber 12. Spray heads with different length tubular portions 144 may be stored in the cart storage bin 108 for accommodating sterilizers of different lengths.

The high pressure pump 60 preferably supplies the cleaning solution to the nozzle 124 at a high pressure (around 2 Kg/sq. cm). This provides the spray with mechanical cleaning action which assists in removing the residue from the chamber walls. The spray head preferably delivers cleaning solution at a pressure of 3.5–85 $Kg/cm^2$, or greater, and at a flow rate of 25–160 liters per minute, or greater.

With reference once more to FIGS. 1 and 5, a second, return fluid line 150 connects the sterilizer chamber 12 with the reservoirs 52, 54 via a second, lower opening 152 (FIG. 6) in the lid plate 83, the outlet strainer 70, and scavenger pump 62, in sequence. While FIG. 1 shows the heater 64 in the inlet line, it is also contemplated that the heater may be positioned in the return line 150, or elsewhere in the system.

The sterilizer includes a drain fitting 164, which is positioned at the lowest point of the sterilizer chamber. The cleaning solution sprayed from the nozzle 124 drips off the walls 10 of the chamber and runs down to the drain fitting. A scavenge fitting 166, at the chamber end of the second fluid line 150 is releasably connected with the drain fitting. The scavenge pump 62 sucks the collected solution from the chamber drain fitting, along the return fluid line and through the filter 70, where large particles of dirt and other debris are removed, which could otherwise cause damage to the pumps or block the nozzle. The returning solution is then heated by the in-line heater 64. A second three way valve 168, such as a directional ball valve, in the return fluid line 150 directs the heated cleaning solution to a selected one of the reservoirs 52, 54.

As for the inlet line 120, a portion 170 of the return line 150 between the lid 80 and the housing is formed from a length of flexible hose which includes quick connect couplings 172A, 174A at first and second ends for quickly connecting with corresponding couplings 172B, 174B on the front panel of the housing and lid 80 respectively. Optionally, the hose reel 134 on the side panel of the housing is also used for storing the hose 170 between use.

An analysis of the residues found on sterilizer walls, by various techniques, such as X-ray Photoelectron Spectroscopy (XPS), has shown that both organic and inorganic substances are present in the residue. To facilitate removal of both types of residue, a two step cleaning process is preferably used. In a first step, an alkaline cleaning solution, which is used to remove organic materials, is sprayed over the chamber walls. In a second step, an acid cleaning solution, which is formulated for removing inorganic materials, is sprayed over the chamber walls 10. The order of the two step process may be reversed, with the acid cleaning step followed by the alkaline cleaning step. However, it is preferable to remove the organic residues first. The two cleaning solutions may be prepared by diluting concentrated cleaning compositions with water or supplied in the dilute form, ready for use.

The first reservoir 52 contains the alkaline cleaning solution 180 and the second reservoir 54 contains the acid cleaning solution 182. The cleaning solutions are withdrawn from the reservoirs through first and second inlet line conduits 184 and 186, which releasably connect the cleaning solution reservoirs 52, 54, respectively, with the first ball valve 136. The inlet line conduits are fluidly connected with siphon tubes 188, 190 inside each of the reservoirs, which extend upward from the lower ends of the reservoirs 52, 54, respectively. Optionally, each siphon tube 188, 190 includes an integral filter 192, 194, respectively, adjacent its lower end, for filtering cleaning solution leaving the reservoir. Optionally, the filter replaces the strainer 68 in the inlet line 120. The first three way valve 136 is switched so as to connect first the alkaline fluid inlet line conduit 184 and, subsequently, the acid fluid inlet line conduit 186 with the high pressure pump 60. Similarly, the cleaning fluid is returned to the reservoirs through first and second return conduits 198 and 200. The second three way valve 168 connects the scavenger pump 62 with the first and second return conduits 198, 200 in turn, to return the alkaline cleaning composition 180 to the alkaline reservoir 52 and subsequently, the acid cleaning composition 182 to the acid reservoir 54. Quick connectors on the conduits 184, 186, 198, 200 connect with corresponding quick connectors on the reservoirs 52, 54 for rapid connection and disconnection of the fluid inlet and outlet lines from the reservoirs.

The reservoirs 52, 54 are of a suitable size for containing sufficient cleaning solution to fill the hoses and conduits during cleaning. For most purposes, a 2–8 gallon tank is a convenient size for each of the reservoirs.

Figure 7:
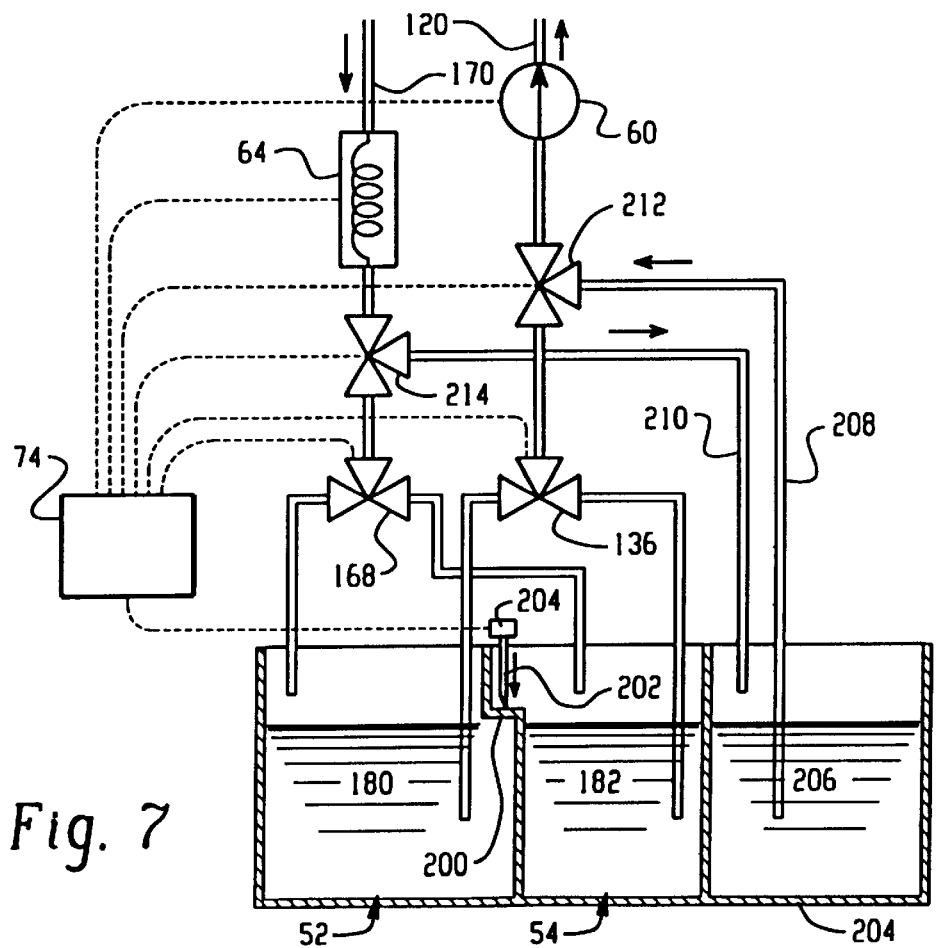
FIG. 7 is a schematic view of an alternative embodiment of part of a cleaning system according to the present invention.

Optionally, as shown in FIG. 7 a third reservoir 204 contains a rinse fluid 206, such as tap water, or distilled water, for removing the cleaning composition from the chamber and from the various hoses, pumps, and conduits, at the end of the cleaning process. Conduits 208 and 210 connect the rinse fluid reservoir 204 with the inlet and return lines 120, 170 via three way valves 212 and 214, respectively. When the three way valves 212, 214 are in a position to direct rinse fluid to and from the chamber, the three way valves 136, 168 are preferably switched to a closed position such that no cleaning solution passes from the reservoirs 52, 54 to the chamber 12.

Alternatively, the rinse inlet conduit 208 is connected with a mains supply of tap water for rinsing the chamber after cleaning. The rinse return conduit 210 is optionally connected with a drain or suitably positioned receptacle. In yet another alternative embodiment, the return valves 168 and 214 are switched to return the used rinse water from the chamber to one of the cleaning fluid reservoirs.

Operation of the various pumps and valves is preferably controlled by the control system 74, which is mounted in the upper housing compartment. The pumps are optionally switched on and off manually, by switches 218 on a control panel 220 conveniently mounted on the outside of the control system. FIG. 2 shows the control panel 220 mounted on the rear housing panel 32, although other convenient locations are also contemplated. Optionally, additional switches 224, shown in FIG. 2 on a side panel, manually operate the ball valves 136, 168, 212, 214. More preferably, the control system 74 operates the switching of the ball valves so that the sterilizer is first cleaned with the alkaline cleaner 180 for a first, preselected time then cleaned with the acid cleaner 182 for a second, preselected time, and finally, rinsed with the rinse fluid 206.

With reference once more to FIG. 2, the operating equipment is preferably powered by electricity, which is supplied through an electrical cord 230 connected to the mains supply of the facility. Alternatively, the equipment may be powered by a battery or a generator mounted on the cart.

The acid and alkaline cleaning solutions 180, 182 are preferably mixed together when cleaning is complete to form a neutral, or near neutral solution which is safe to dispose of in a sanitary sewer system, without further treatment. By near neutral, it is meant that the cleaning solutions, when combined, have a pH of 6 to 8, more preferably, a pH of 6.5 to 7.5. Accordingly, the volumes, and or the pH of the two cleaning solutions used are preferably selected such that, when mixed, a near neutral solution is formed.

In one embodiment, shown in FIG. 7, a connecting portion or wall 200, which forms a barrier between the first and second reservoirs 52, 54, is opened after cleaning to allow the two cleaning solutions to mix. The mixing results in the formation of a neutral, or near neutral composition. Various opening mechanisms are contemplated. In one preferred embodiment, an opening member, such as a cutter 202 cuts the connecting wall between the two reservoirs to allow mixing. The opening member is preferably actuated by an actuator 204, such as a solenoid valve, which is operated by the control system 74. In another embodiment, a valve (not shown) is opened to allow cleaning solution to pass between the two reservoirs.

In another alternative embodiment, the alkaline reservoir 52 is sized to accommodate both the acid and the alkaline cleaning solutions 180, 182. At the end of the acid cleaning portion of the cleaning cycle, the return ball valve 168 is switched so that the acid cleaning solution 182 is directed into the alkaline reservoir 52. The high pressure pump and scavenger pumps 60, 62 continue to pump the acid cleaning solution from the acid reservoir 54 until all the acid cleaning solution has passed through the chamber 12 and into the alkaline reservoir, where it mixes with the alkaline cleaning solution. This method of circulation can also be used to enhance mixing when a barrier 200 between the two reservoirs is opened, as described above.

In operation, fresh reservoirs 52, 54 of cleaning solution are loaded into the lower compartment 39 of the cart 20 and the quick connectors on the conduits 186, 184, 198, 200 connected with the corresponding connectors on the reservoirs. The cart is then wheeled through the facility and positioned adjacent to the sterilizer to be cleaned. The electric cord 230 is connected to a suitable mains outlet. A suitably sized lid 80 and nozzle attachment 124 are selected and connected together by quick connect fitting 133B. A door 232 to the sterilizer is opened and the lid 80 clamped to the end ring 84 of the chamber to seal the opening 82, as shown in FIG. 6. Quick connections 174, 172 are made between the return hose 170 and the drain fitting 166 and the housing 22, respectively. Similarly, quick connections 132, 130 are made to connect the inlet hose 128 with the nozzle 124 and the housing, respectively. The pumps 60, 62 are switched on and the heater 64 begins to heat the alkaline cleaning solution to the desired temperature for cleaning. Heating is continued while the alkaline cleaning solution is circulated through the chamber until the desired cleaning temperature is reached. Heating is continued, as needed, to maintain the temperature.

The three way valves 136,168 are set by the controller 74, or set manually, so that the alkaline cleaning solution 180 is pumped along the fluid inlet line 120 to the nozzle 124 by the high pressure pump 60 and the sprayed cleaning solution is returned to the same tank 52 along the fluid return line 150 by the scavenger pump 62.

The scavenger pump 62 operates to maintain a slight negative pressure in the chamber. This assists in keeping the lid 80 in a sealing relation with the end ring 84 and ensures that the sprayed cleaning solution is removed quickly from the bottom of the chamber. The bottom of the chamber is the area of the chamber where the cleaning solution and residue tends to accumulate. It is, therefore, desirable to prevent the cleaning solution from pooling there and inhibiting the mechanical cleaning action of the spray. Residues which are carried from the chamber into the tank 52 are filtered from the recirculating cleaning solution by the return strainer 70 so that they do not clog the nozzle spray head 142 and other parts of the equipment.

After a period of cleaning, typically 1–2 hours for heavily encrusted residue, or less for lightly soiled chambers, the high pressure pump 60 is switched off temporarily while the first (alkaline) cleaning solution 180 remaining in the chamber and fluid lines is returned to the first tank 52. The three way valves 136,168 are then switched so that the second cleaning solution (acid) 182 is circulated through the chamber in the same manner as described above for the alkaline cleaning solution 180. This is continued for a period sufficient to remove remaining, inorganic residue from the chamber, typically 1–2 hours for heavily soiled chambers, or less for lightly soiled chambers. Since the cleaning solutions do not significantly influence the nickel plating on the chamber walls, the cleaning process may be further extended to ensure thorough cleaning.

The chamber walls are cleaned and passivated in the cleaning process. Passivation is the reduction in the tendency of a metal to corrode. Passivity may result from the formation of a thin semiconducting oxide film on the metal surface (termed chemical passivity) or the precipitation of solid salts to form a thicker, but porous layer (termed mechanical passivity). Oxidizing agents, such as phosphoric acid, are capable of passivating iron and steel chambers.

During the cleaning of the chamber interior 12, the chamber door 232, in cases where it is not cleaned by the process, may be cleaned by conventional cleaning methods, such as hand cleaning. Alternatively, a replaceable cover for the interior of the door is conveniently replaced at this time.

At the end of the cleaning process, the connecting portion 200 between the two tanks 52, 54 is opened and the cleaning solutions allowed to mix, and/or other mixing methods, as described above, are employed. Optionally, the mixed cleaning solution is circulated through the chamber 12 and fluid lines 120, 150 to neutralize remaining cleaning solutions thereon.

Alternatively, or additionally, a rinse cycle is used to wash the chamber and hoses. Rinse fluid 206 is pumped by the high pressure pump 60 through the inlet fluid line 120 to the nozzle 124 and returned by the scavenger pump 62 to one of the cleaning solution tanks, the rinse tank 204, or to a drain or other receptacle. In this way, the hoses can be handled safely without risk of drops of cleaning solution falling on the technician or outside the chamber. The quick connectors on the two tanks 52, 54 are then disconnected from the corresponding conduits and the tanks emptied into the sanitary sewer system, or transported to a disposal facility.

The air bleed valve 106 is opened to allow air to enter through the air line 104 into the sterilizer chamber to equalize the pressure inside the chamber. The lid 80 is then unclamped from the sterilizer end ring 84. The lid 80, nozzle 124, and hoses 128,170 are uncoupled and stored on the cart 20.

The entire cleaning process is readily completed in 2–4 hours, much faster than for conventional cleaning methods. Additionally, since the solid state control 74 controls many or all of the operations of the cleaning process, the technician is free to perform other servicing functions during the cleaning time.

If desired, the acid and alkaline cleaning steps may be repeated one or more times, for example, if the sterilizer chamber is heavily encrusted with deposits. Fresh cleaning solutions may be used for each repeated cleaning step. Or, the same solutions may be reused.

Figure 8:
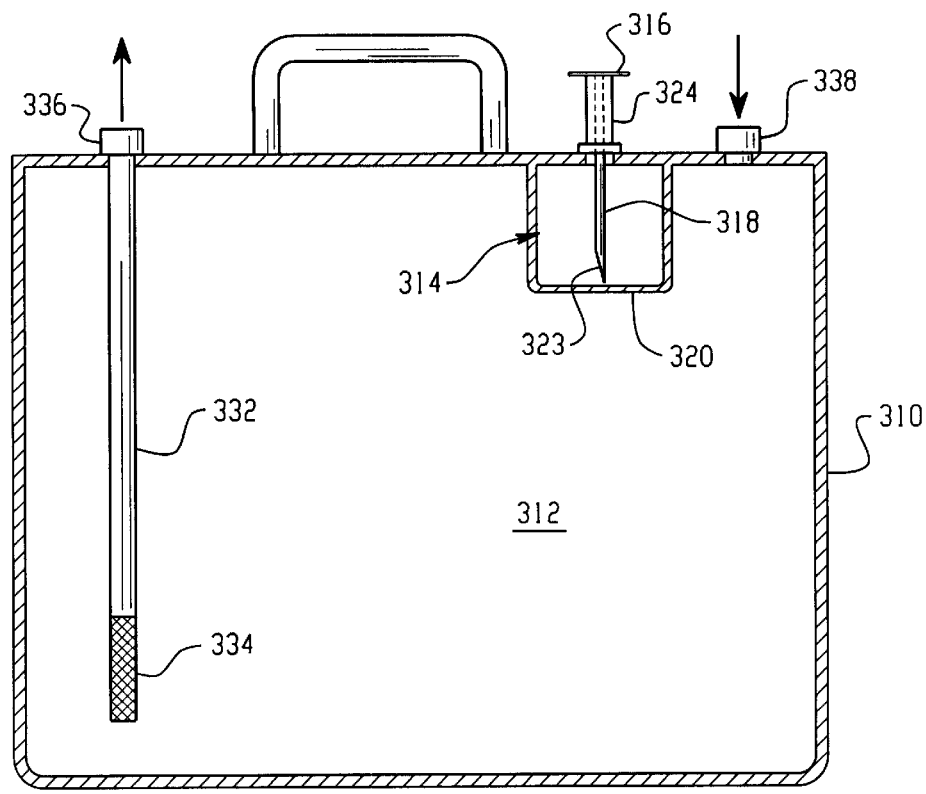
FIG. 8 is an alternative embodiment of a cleaning solution supply tank in accordance with the present invention.

In yet another embodiment, shown in FIG. 8, a single reservoir 310 replaces the two cleaning solution reservoirs 52, 54 and includes a first chamber 312 which receives a cleaning solution suitable for removing all types of deposits from the sterilizer. Such a system is used, for example, when the deposits from the sterilizer are easier to remove, or are relatively less heavily accreted, or is used at intervals, in between major two-reservoir cleaning processes, to keep deposit buildup to an acceptable level. In this embodiment, a neutralizing chamber 314 is separately formed in the reservoir for receiving a neutralizing agent. The neutralizing agent is a chemical which reacts with the cleaning solution to form a non-hazardous substance which may be disposed in the sanitary sewer system, or otherwise safely disposed. For example, if the cleaning solution is acidic, the neutralizing agent is alkaline, and vice versa.

After cleaning is complete, an actuator 316 causes an opening member 318, such as a cutter, to pierce a connecting wall 320 between the neutralizing chamber and the cleaning solution chamber. The neutralizing agent mixes with the used cleaning solution to form a neutral solution. The actuator 316 may be a solenoid valve, operated by a control system, as described above, or a manual actuator, as shown in FIG. 8. A simple actuator, which is disposable along with the reservoir, includes a compressible tube 324, formed from paper, plastic, or the like which houses an upper end of the cutter. The tube 324 inhibits accidental actuation of the cutter prior to and during cleaning. A lower end of the cutter, which defines a cutting edge or blade 323 or other suitable cutting shape, is positioned in the neutralizing chamber (or, alternatively, in the cleaning solution chamber), adjacent the connecting wall 320. An operator presses an upper end of the tube 324, crushing the tube and depressing the cutter 318 until the cutting edge 323 cuts the connecting wall 320.

A siphon tube 332 includes an integral filter 334 for filtering cleaning solution leaving the reservoir. Optionally, the filter replaces the strainer in the inlet line. The syphon tube is connected with an inlet line quick connector 336 for quickly connecting the syphon tube with the inlet line. A return quick connector 338 couples a return line with the cleaning solution chamber 312. The operating equipment and cart used in this embodiment are essentially as shown in FIGS. 1 and 2. However, the ball valves 136 and 168 are preferably eliminated in this embodiment or replaced with simple open and shut type valves.

Figure 9:
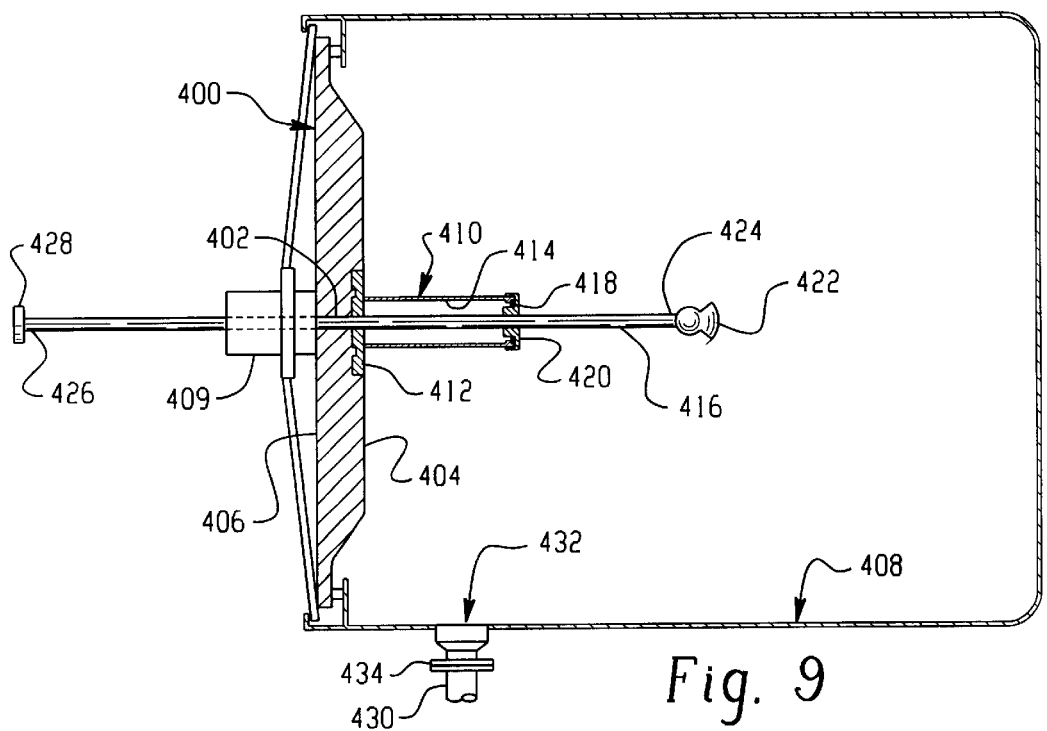
FIG. 9 is a schematic view of a part of a cleaning system in position on a sterilizer, in accordance with another embodiment of the present invention.

With reference to FIG. 9, an embodiment of the system suitable for use in sterilizers having a door 400 with a generally centrally positioned opening 402, passing through the door, is shown. This embodiment takes advantage of the readily available central opening to supply cleaning fluid to the chamber. Certain sterilizers, particularly larger models of the radial arm type, have a closure mechanism (not shown) which makes use of the central opening. In such cases, parts of the closure mechanism are readily removable. For example, in the case of an Amsco brand 24×36 radial arm sterilizer, the door diaphragm cover, diaphragm, and clutch rod assembly are first removed from the inside 404 of the door. On the outside 406 of the door, the door handwheel and clutch lock cap are then removed, thereby providing an opening 402 with access to the sterilizer chamber 408 from the outside of the sterilizer. Parts of the door mechanism 409, which do not obstruct the opening, are left in position on the door. This embodiment allows the inside of the door to be cleaned at the same time as the chamber walls, without the need for separate, hand cleaning.

Once the appropriate parts of the closure mechanism have been removed, an adapter 410, is fitted to the inside (or to the outside) of the door. The adapter has an attachment portion 412, which is suitably shaped for interconnection with the door around the opening, for example by means of a screw thread, clamp, or other method of attachment. A horizontally extending bore 414 is defined through the adapter with an internal diameter sufficient to receive an inlet tube 416 therethrough. The inlet tube thus passes through the opening 402 in the door and into the chamber interior. The inlet tube is conveniently formed from a length of ⅜" stainless steel or rigid plastic pipe, or other rigid material which is resistant to the cleaning fluids used. A seal 418, such as an O-ring, provides a leak-tight seal between the tube and the bore. The seal may be held in place by a nut 420 threaded into one end of the inlet tube. Other methods of sealing the inlet tube to the adaptor are also contemplated, including welding of the inlet tube to the adapter bore 414.

A nozzle 422 is attached to an inner end 424 of the tube 416 for spraying cleaning fluid over the walls of the chamber and the inner surface of the door. The length of the inlet tube is selected so as to position the nozzle so that the cleaning fluid reaches all the walls of the chamber and the inner surface of the door during the cleaning process.

An outer end 426 of the inlet tube is connected with the cleaning fluid supply reservoirs 52, 54, in a similar manner to that shown in FIG. 1. For example, the outer end may include a quick connect coupling 428 which couples with a corresponding quick connect coupling at the end of the flexible hose 128 (shown in FIG. 1). Alternatively, the inlet tube may be connected with a single reservoir of the type illustrated in FIG. 8.

An outlet line 430, for withdrawing the sprayed cleaning fluid from the chamber, may be connected to a lower end of the chamber through a second opening in the sterilizer chamber 408. The outlet line 430 is connected to a separate outlet 432 at a lower end of the sterilizer, by quick connects 434, or other suitable connectors, as shown in FIG. 9.

Figure 10:
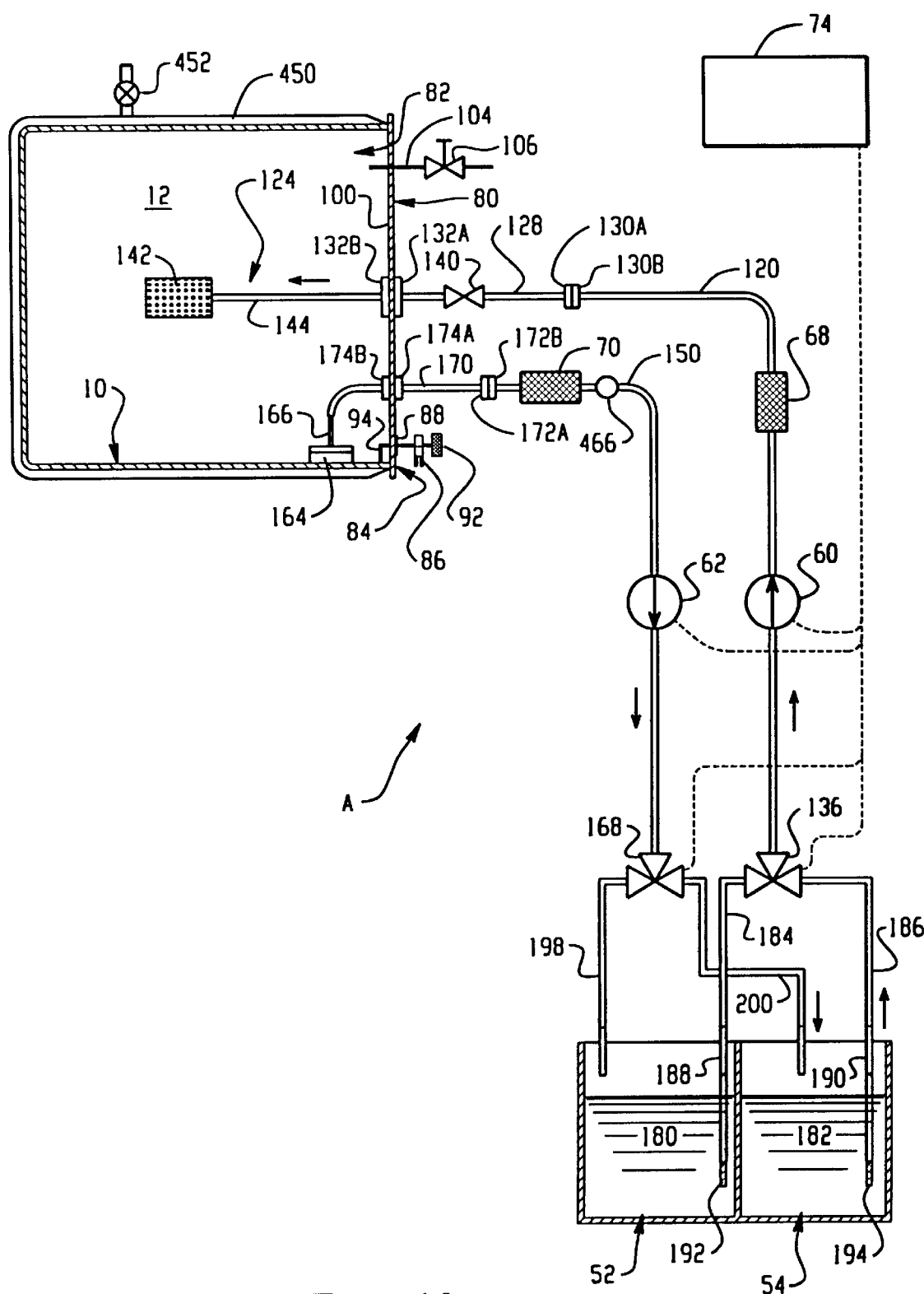
FIG. 10 is an a schematic view of an alternative cleaning system in position on a sterilizer, in accordance with another embodiment of the present invention.

FIG. 10 shows an alternative embodiment of the system, in which the in-line heater 64 is omitted. In this embodiment, the cleaning solution is heated in the sterilizer by employing the sterilizer's own heating system 450. For example, the sterilizer of FIG. 1 is surrounded by a steam jacket 450. The steam jacket is supplied with steam through a valve 452 while the cleaning solution is circulated through the chamber 12. When a sensor 466 displays that the cleaning solution is at the selected temperature for effective cleaning, the steam supply to the steam jacket 450 is switched off by closing the valve. If the sensor subsequently registers that the temperature of the cleaning solution is below an acceptable level, the steam supply may be recommenced.

In this embodiment, it is preferable for the temperature sensor 466 to be positioned in the return line 170, where it measures the temperature of the cleaning solution just after it leaves the chamber 12. The control system 60, in this embodiment, does not control the addition of steam to the sterilizer, although it is also contemplated that the sterilizer may be modified so that the control system controls the opening of the steam valve 452 automatically, in response to detected solution temperatures received from the sensor 466.

Cleaning Compositions

The acidic cleaning solution 182 includes an acid component and preferably also includes a surfactant, a chelating polymer, and the balance water.

The acid component is preferably a strong acid, having a low pH (preferably about pH 0–3, more preferably, 0–2 for a 0.1M aqueous solution of the acid). Suitable acid components include phosphoric acid, hydroxyacetic acid (glycolic acid), and sulfamic acid. Phosphoric acid, which has a passivating effect on stainless steel, is particularly preferred. The acid component is preferably present at the concentration of about 14–55%, more preferably, present at a concentration of about 40–50% weight, most preferably at about 45–48% by weight of the acidic cleaning solution. The acid component can be a combination of two or more acids. For example, a cleaner containing about 42% phosphoric acid (readily formed by using 60% of a 70% W/W phosphoric acid solution) and about 5% by weight citric acid is particularly effective.

The surfactant is selected from the group consisting of anionic, cationic, nonionic, and zwitterionic surfactants to enhance cleaning performance. Examples of such surfactants include water soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid esters of 1,2 dihydroxypropane sulfonates, and the substantially saturated higher aliphatic acyl amides of lower aliphatic amino carboxylic acid compounds, such as those having 12–16 carbons in the fatty acid, alkyl, or acyl radicals, and the like. Examples of the last mentioned amides are N-lauroyl, N-miristoyl, or N-palmitoyl sarcosines.

Additional examples are condensation products of ethylene oxide with various reactive hydrogen compounds reactive therewith having long hydrophobic chains (e.g. aliphatic chains of about 12–20 carbon atoms), which condensation products ("ethoxamers") contain hydrophilic polyethylene moieties, such as condensation products of poly(ethylene oxide) with fatty acids, fatty alcohols, fatty amides, polyhydric alcohols (e.g. sorbitan monostearate), and polypropyleneoxide (e.g. pluronic materials).

Particularly preferred surfactants are low foaming amphoteric surfactants or anionic surfactants (generally not low foaming), either alone, or in combination with non-ionic surfactants. Miranol JEM, an amphocarboxylate, short chain, low foaming surfactant obtainable from Rhone-Poulenc as a 45% by weight solution is a typical suitable surfactant. The surfactant is present in the cleaning solution at a concentration of about 0.1–5.0% by weight, more preferably, around 0.2–3.0%, most preferably, at about 0.3% by weight.

The polymer is preferably one which is stable in the acid conditions. Suitable polymers include acrylamides, polyacrylates, and other chelating polymers, alone or in combination. One suitable polymer is TRC 233i, an acrylamide-type polymer obtainable from Calgon Corporation. The polymer is preferably at a concentration of 0.2–10% by weight, more preferably, around 0.2–2.0%, most preferably, at around 1% by weight of the acid cleaning solution.

Water suitable for the present invention can be distilled water, soft water, or hard water. Soft water is preferred.

A preferred acid cleaning solution includes, in terms of weight percent.

| Component | Weight % | Preferred weight % |
|---|---|---|
| Phosphoric acid | 14–55 | 45–48 |
| Citric Acid | 0–10 | 2–8 |
| Surfactant | 0.1–5 | 0.2–3 |
| Polymer | 0–10 | 0.2–2 |
| Water | Q.S. | |

The alkaline cleaning solution 180 includes an alkaline component and preferably also a surfactant, a chelating agent, and the balance water.

The alkaline component is preferably a strong base, having a high pH (preferably, pH 13–14 for a 0.1M solution of the base), such as sodium hydroxide or potassium hydroxide, or a combination thereof. Other suitable alkaline components include quaternary ammonium hydroxides, such as alkyl quaternary ammonium hydroxides, including tetramethyl ammonium hydroxide, tetraethyl ammonium hydroxide, and the like. The alkaline component is preferably present at a concentration of 10–30%, more preferably, at around 20–25% by weight. A particularly preferred alkaline cleaning composition includes 21.0% potassium hydroxide (readily prepared by using 47% by weight of 45% W/W potassium hydroxide solution).

The surfactant is preferably as described for the acid cleaning solution. A preferred alkaline cleaning solution includes Miranol JEM. The surfactant is preferably at a concentration of 0.4–5%, and more preferably, about 0.9% by weight of the alkaline cleaning solution. For example, a 0.9% concentration can be achieved using 2% Miranol JEM (since this is a 45% solution).

The chelator is present at a concentration of from about 3–20% of the alkaline cleaning composition 180. It preferably includes a polyacrylic acid, at a concentration of 0.1 to 3% by weight, more preferably, at around 0.3% by weight of the alkaline cleaning composition. The chelator may also include sodium gluconate at a concentration of 1–7%, more preferably, at around 4–5%, most preferably, at around 5% by weight of the alkaline cleaning solution. The chelator may also include EDTA or a salt thereof at a concentration of 2–6%, more preferably at around 2–4%, most preferably, at about 4% of the alkaline cleaning composition.

Optionally, the alkaline cleaning composition 180 may include more than one alkaline component, more than one surfactant, and more than one chelating agent.

A preferred alkaline cleaning solution 180 includes, in terms of weight percent.

| Component | Weight % | Preferred weight % |
| --- | --- | --- |
| Potassium hydroxide | 10–30 | 20–25 |
| Sodium Gluconate | 0–7 | 4–5 |
| Sodium EDTA | 0–6 | 2–4 |
| Surfactant | 0.4–5 | about 0.9 |
| Polyacrylic acid | 0.1 to 3 | about 0.3 |
| Soft Water | Q.S. | |

The two step cleaning system (one acid, one alkaline) thus described cleans and passivates the sterilizer chamber. Alternatively, one or other of the alkaline and acid cleaning solutions may be used in the single reservoir 310 of FIG. 8.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for removing baked on residues from a sterilizer chamber, the apparatus comprising:
   a supply of cleaning fluid;
   a lid for closing an opening to the sterilizer;
   a nozzle mounted to the lid for spraying the cleaning fluid into the chamber, the sprayed cleaning fluid removing baked on residues from the sterilizer chamber;
   a first fluid supply line fluidly connecting the supply of cleaning fluid with the nozzle;
   a first pump fluidly connected with the first fluid line for pumping the cleaning fluid to the chamber;
   a second pump for pumping the cleaning fluid from the chamber.

2. The apparatus of claim 1, further including:
   a movable cart, the cart including:
      a storage bin for holding a plurality of interchangeable lids of different sizes.

3. The apparatus of claim 1, wherein the nozzle delivers the cleaning fluid at a pressure of from 3.5 to 85 Kg/cm$^2$.

4. The apparatus of claim 1, wherein the nozzle includes:
   an articulating spray head which is powered by pressure of the cleaning fluid entering the nozzle.

5. The apparatus of claim 4, wherein the spray head articulates about three axes.

6. The apparatus of claim 1 further comprising:
   a moveable cart which carries the supply of cleaning fluid and the first pump;
   an outlet in the lid through which sprayed cleaning fluid can be withdrawn from the chamber;
   a second fluid supply line fluidly connected with the outlet, the second pump being carried by the cart and fluidly connected with the second fluid line for removing the cleaning fluid from the chamber.

7. The apparatus of claim 6, wherein the second fluid line is connected with the supply of cleaning fluid.

8. The apparatus of claim 6, wherein the supply of cleaning fluid includes:
   a reservoir of a first cleaning fluid; and
   a reservoir of a second cleaning fluid;
   the apparatus further including:
      a first three way valve for selectively connecting one of the reservoir of the first cleaning fluid and the reservoir of the second cleaning fluid with the first fluid line, and
      a second three way valve for selectively connecting the second fluid line with one of the reservoir of the first cleaning fluid and the reservoir of the second cleaning fluid.

9. The apparatus of claim 8, further including a source of rinse fluid which is carried by the cart and is fluidly connected with the nozzle.

10. The apparatus of claim 6, further including:
    a heater carried by the cart for heating the cleaning fluid, the heater being fluidly connected with one of the first fluid line and the second fluid line.

11. An apparatus for removing baked on organic residues and inorganic residues from a chamber, the apparatus comprising:
    a first cleaning fluid reservoir which holds a first cleaning fluid for removing organic residues;
    a second cleaning fluid reservoir which holds a second cleaning fluid for removing inorganic residues and passivating the chamber;
    a nozzle for spraying the cleaning fluid into the chamber, the sprayed cleaning fluid removing baked on organic residues and inorganic residues from the chamber;
    a first fluid supply line fluidly connecting the first and second cleaning fluid reservoirs of cleaning fluid with the nozzle;
    a first pump fluidly connectable with the nozzle and the first and second cleaning fluid reservoirs for pumping the cleaning fluid to the chamber;
    a second pump fluidly connectable with the chamber for pumping the cleaning fluid from the chamber.

12. The apparatus of claim 11, further including a lid mountable across an opening to the chamber, the lid having an aperture, the nozzle being connectable with the lid such that the nozzle is fluidly connectable with the first pump through the lid aperture.

13. The apparatus of claim 11, wherein the chamber includes a door for closing an opening to the chamber, the door having a central aperture, the nozzle being mountable to the door adjacent the aperture such that the door aperture fluidly connects the first pump with the nozzle.

14. A method of removing baked on residues from a sterilizer chamber, the method comprising:
    mounting a lid over an opening to the chamber such that a nozzle mounted to the lid extends into an interior of the chamber:
       pumping a first cleaning fluid from a first source of cleaning fluid to the nozzle;
       spraying the first cleaning fluid from the nozzle over walls of the chamber to remove baked on residues from the chamber walls;

pumping the sprayed first cleaning fluid from the chamber.

15. The method of claim 14, wherein the lid is provided by a door of the chamber, which selectively closes the chamber opening, the door having an aperture formed therein.

16. The method of claim 14, wherein pumping the sprayed cleaning fluid from the chamber includes:
returning the sprayed first cleaning fluid to the first source of cleaning fluid.

17. The method of claim 14, wherein pumping the sprayed first cleaning fluid from the chamber is carried out simultaneously with pumping a first cleaning fluid from the first source of cleaning fluid to the nozzle and at a sufficient rate to create a negative pressure within the chamber.

18. The method of claim 14, wherein spraying the first cleaning fluid from the nozzle over walls of the chamber includes spraying the first cleaning fluid at a pressure of from 3.5 to 85 Kg/cm$^2$.

19. The method of claim 14, wherein spraying the first cleaning fluid from the nozzle over walls of the chamber includes:
spraying the first cleaning fluid from an articulating spray head which is powered by pressure of the first cleaning fluid entering the nozzle.

20. The method of claim 19, wherein the spray head articulates about three axes.

21. The method of claim 14, further including:
transporting pumps for pumping the cleaning fluid to and from the chamber and the cleaning fluid supply to the sterilizer on a moveable cart.

22. A method of removing baked on residues from a sterilizer chamber, the method comprising:
mounting a lid over an opening to the chamber such that a nozzle mounted to the lid extends into an interior of the chamber:
pumping a first cleaning fluid from a first source of cleaning fluid to the nozzle;
spraying the first cleaning fluid from the nozzle over walls of the chamber to remove baked on residues from the chamber walls;
pumping the sprayed first cleaning fluid from the chamber;
after pumping the first cleaning fluid to the nozzle, spraying the first cleaning fluid from the nozzle over walls of the chamber, and pumping the sprayed first cleaning fluid from the chamber:
pumping a second cleaning fluid from a second source of cleaning fluid to the nozzle;
spraying the second cleaning fluid from the nozzle over the walls of the chamber;
pumping the sprayed second cleaning fluid from the chamber; and
spraying a rinse fluid from the nozzle over the walls of the chamber.

23. The method of claim 22, further including, after pumping the second cleaning fluid to the nozzle, spraying the second cleaning fluid over the walls of the chamber, and pumping the sprayed second cleaning fluid from the chamber:

mixing the first and second cleaning fluids together to form a solution of neutral or near neutral pH.

24. The method of claim 23, wherein:
the first cleaning fluid is formulated for removing organic residues from the chamber walls; and
the second cleaning fluid is formulated for removing inorganic residues from the chamber walls.

25. The method of claim 24, wherein:
the first cleaning fluid is an alkaline cleaning fluid; and
the second cleaning fluid is an acid cleaning fluid.

26. The method of claim 22, wherein:
pumping and spraying the first cleaning fluid include continuously recirculating the first cleaning fluid through the chamber for a period of about 1 to 2 hours; and
pumping and spraying the second cleaning fluid include continuously recirculating the second cleaning fluid through the chamber for a period of about 1 to 2 hours.

27. The method of claim 22, wherein one of the first and second cleaning fluids includes an acid which removes baked on inorganic residues from the chamber and the other of the first and second cleaning fluids includes an alkali which removes baked on organic residues from the chamber.

28. An apparatus for removing baked on residues from a sterilizer chamber, the apparatus comprising:
means for mounting a lid over an opening to the chamber such that a nozzle mounted on the lid extends into an interior of the chamber;
a means for pumping a first cleaning fluid from a first source of cleaning fluid to the nozzle such that the nozzle sprays the first cleaning fluid over walls of the chamber, thereby removing baked on residues from the walls of the chamber; and,
a means for pumping the sprayed first cleaning fluid from the chamber.

29. An apparatus for removing baked on residues from a sterilizer chamber, the apparatus comprising:
a reservoir of an alkaline cleaning fluid;
a reservoir of an acid cleaning fluid;
a lid configured to close and seal an opening to the sterilizer;
a nozzle mounted to the lid which sprays the acid and alkaline cleaning fluids into the chamber, the sprayed cleaning fluids removing baked on residues from the sterilizer chamber;
a first fluid supply line selectively fluidically connects each of the reservoirs with the nozzle;
a second fluid supply line carries the cleaning fluids from the chamber;
a pump pumps the acid and alkaline cleaning fluids from the chamber through the second fluid supply line.

* * * * *